United States Patent
Bhargava

(10) Patent No.: US 9,616,080 B2
(45) Date of Patent: *Apr. 11, 2017

(54) EDIBLE ENERGY COMPOSITION

(71) Applicant: International IP Holdings LLC, Bloomfield Hills, MI (US)

(72) Inventor: Manoj Bhargava, Farmington Hills, MI (US)

(73) Assignee: INTERNATIONAL IP HOLDINGS LLC, Bloomfield Hills, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/838,525

(22) Filed: Aug. 28, 2015

(65) Prior Publication Data

US 2015/0366891 A1 Dec. 24, 2015

Related U.S. Application Data

(63) Continuation of application No. 14/144,704, filed on Dec. 31, 2013, now Pat. No. 9,119,413, which is a continuation of application No. 13/364,795, filed on Feb. 2, 2012, now Pat. No. 8,632,834, which is a continuation of application No. 12/139,163, filed on Jun. 13, 2008, now Pat. No. 8,187,647.

(51) Int. Cl.
| | |
|---|---|
| *A23L 2/38* | (2006.01) |
| *A61K 31/7068* | (2006.01) |
| *A61K 9/00* | (2006.01) |
| *A61K 31/185* | (2006.01) |
| *A61K 31/198* | (2006.01) |
| *A61K 31/365* | (2006.01) |
| *A61K 31/455* | (2006.01) |
| *A61K 31/519* | (2006.01) |
| *A61K 31/522* | (2006.01) |
| *A61K 31/675* | (2006.01) |
| *A61K 31/714* | (2006.01) |
| *A23L 27/30* | (2016.01) |
| *A23L 33/00* | (2016.01) |
| *A23L 33/10* | (2016.01) |
| *A23L 33/15* | (2016.01) |
| *A23L 33/175* | (2016.01) |

(52) U.S. Cl.
CPC .......... *A61K 31/7068* (2013.01); *A23L 27/37* (2016.08); *A23L 33/10* (2016.08); *A23L 33/15* (2016.08); *A23L 33/175* (2016.08); *A23L 33/40* (2016.08); *A61K 9/0053* (2013.01); *A61K 31/185* (2013.01); *A61K 31/198* (2013.01); *A61K 31/365* (2013.01); *A61K 31/455* (2013.01); *A61K 31/519* (2013.01); *A61K 31/522* (2013.01); *A61K 31/675* (2013.01); *A61K 31/714* (2013.01); *A23V 2002/00* (2013.01)

(58) Field of Classification Search
CPC .... A23L 1/0325; A23L 1/2367; A61K 31/522
USPC .............................. 426/590, 656, 72, 73, 650
See application file for complete search history.

(56) References Cited

U.S. PATENT DOCUMENTS

| 5,397,786 A | 3/1995 | Simone |
| 5,760,005 A | 6/1998 | Iwatschenko et al. |
| 2001/0043957 A1 | 11/2001 | Mann |
| 2002/0102345 A1 | 8/2002 | Ramirez |
| 2002/0176881 A1 | 11/2002 | Verlaan et al. |
| 2003/0219500 A1 | 11/2003 | Howard et al. |
| 2004/0096547 A1 | 5/2004 | Ferruzzi |
| 2005/0031651 A1 | 2/2005 | Gervais et al. |
| 2006/0286181 A1 | 12/2006 | Gardiner et al. |
| 2007/0224292 A1 | 9/2007 | Brunner et al. |

FOREIGN PATENT DOCUMENTS

| JP | 2005527234 A1 | 9/2005 |
| WO | WO8808259 A1 | 11/1988 |
| WO | WO03079818 A1 | 10/2003 |
| WO | WO2005018344 A1 | 8/2005 |
| WO | WO2006112283 A1 | 10/2006 |

OTHER PUBLICATIONS

Flashup Drink, Disclosure from the Russian Patent Office 1999.
International Report on Patentability for WO2009065119, Nov. 17, 2008.
Driskell et al, Sports Nutrition:Vitamins and Trace Elements, Second Edition. 2006, pp. 146-148.
Wikipedia "Red Bull" http://en.wikipedia.org/wiki/Red_Bull, 2009.
5-Hour Energy Ingredients & Safety, 2011, http://www.5hourenergy.com/ingredients.asp, pp. 1-3.
Frequently Asked Questions about 5-Hour Energy, http://www.5hourenergy.com/QandA.asp, pp. 1-3, 2011.

*Primary Examiner* — Helen F Heggestad
(74) *Attorney, Agent, or Firm* — Oakland Law Group PLLC

(57) ABSTRACT

An energy composition includes a methylated xanthine, a choline derivative, and at least one flavorant in a sufficient amount to render the energy composition palatable. The energy composition may also include vitamins, amino acids, preservatives, and the like.

13 Claims, No Drawings

EDIBLE ENERGY COMPOSITION

CROSS-REFERENCE TO RELATED APPLICATION

This application is a continuation of U.S. patent application Ser. No. 14/144,704, now U.S. Pat. No. 9,119,413, filed Dec. 31, 2013 which is a continuation of Ser. No. 13/364,795, now U.S. Pat. No. 8,632,834, filed Feb. 2, 2012, which is a continuation of U.S. patent application Ser. No. 12/139,163, now U.S. Pat. No. 8,187,647, filed Jun. 13, 2008 all of which are incorporated by reference herein.

BACKGROUND OF THE INVENTION

1. Field of the Invention

The present invention relates to edible compositions that provide an individual with an energy burst when consumed.

2. Background Art

Energy drinks are beverages that provide an individual with an energy surge that lasts for a variable period of time. Coffee, which is perhaps the best known energy drink, derives most of its energy enhancing properties from caffeine. Recently, there has been an increase in the number of soft drinks that also provide an energy boost that is equal to or superior to coffee. In addition, such energy drinks may also include sugar which also provides a transient increase in an individual's perceived energy levels.

Many different formulations for energy drinks exist. However, not all existing formulations are palatable to all consumers. Some of the prior art formulations possess an unpleasant taste due to the constituents. Other formulations fail to provide a sufficient energy burst. Moreover, consumers continually desire unique and healthy formulations.

Accordingly, there is a need for improved edible compositions for providing an individual with a perceived energy boost.

SUMMARY OF THE INVENTION

The present invention solves one or more problems of the prior art by providing an edible energy composition. The energy composition of this embodiment includes a methylated xanthine, a choline derivative, and at least one flavorant in a sufficient amount to render the energy composition palatable. The combination of the methylated xanthine and the choline derivative promotes a more rapid occurrence of the stimulating effects of the choline derivative. Normally, choline derivatives require consumption over several days before the effects of such derivative are observed. Advantageously, the stimulating effects of the present embodiment occur within minutes or hours of consumption. The energy composition may also include vitamins, amino acids, preservatives, and the like.

In another embodiment, an edible energy composition comprises caffeine in an amount from about 0.0037 mg/ml to about 0.0039 mg/ml, citicoline in an amount from about 0.0004 mg/ml to about 0.0006 mg/ml, amino acids or an amino acid derivative in an amount from about 0.01 to about 0.03 mg/ml, vitamins in an amount from about 0.0010 to about 0.0025 mg/ml, glucuronolactone is present in an amount from about 0.005 to about 0.007 mg/ml, and at least one flavorant in a sufficient amount to render the energy composition palatable.

In yet another embodiment, an edible energy composition comprises caffeine in an amount from about 0.0032 g/ml to about 0.0034 g/ml, citicoline in an amount from about 0.00015 g/ml to about 0.00019 g/ml, amino acids or an amino acid derivative in an amount from about 0.01 to about 0.03 mg/ml, vitamins in an amount from about 0.0010 to about 0.0025 mg/ml, glucuronolactone is present in an amount from about 0.005 to about 0.007 mg/ml, and at least one flavorant in a sufficient amount to render the energy composition palatable.

DETAILED DESCRIPTION OF THE PREFERRED EMBODIMENT(S)

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

The following description of the embodiment(s) is merely exemplary in nature and is in no way intended to limit the invention, its application, or uses.

In an embodiment of the present invention, an edible energy composition is provided. The energy composition includes water and a combination of at least two stimulants. In a variation of this embodiment, the energy composition includes a methylated xanthine and a choline derivative. Examples of methylated xanthines, include but are not limited to caffeine and theobromine. Caffeine is particularly useful in the practice of the present invention. In a refinement of the present embodiment, the methylated xanthine is present in an amount from about 0.0005 g/ml to about 0.005 g/ml. In another refinement of the present invention, the methylated xanthine is present in an amount from about 0.0035 g/ml to about 0.0045 g/ml. In still another embodiment of the present embodiment, the methylated xanthine is present in an amount from about 0.0037 g/ml to about 0.0039 g/ml. In yet another refinement of the present embodiment, the methylated xanthine is present in an amount from about 0.0032 g/ml to about 0.0034 g/ml.

Variations of the present invention also include a choline. A particularly useful choline is citicoline which is a well-known brain enhancer. Brain enhancers are substances that are known to improve an individual's mental acuity. In a refinement, the choline derivative is present in an amount from about 0.00005 g/ml to about 0.0009 g/ml. In another refinement, the choline derivative is present in an amount from about 0.0003 g/ml to about 0.0007 g/ml. In still another refinement, the choline derivative is present in an amount from about 0.0004 g/ml to about 0.0006 g/ml. In still another refinement, the choline derivative is present in an amount from about 0.00015 g/ml to about 0.00019 g/ml.

In a variation of the present embodiment, the energy composition further comprises one or more vitamins. Examples of such vitamins include, but are not limited to B6, B12, niacinamide, niacin, folic acid, and the like. In a refinement, vitamins are present in an amount from about 0.0005 g/ml to about 0.008 g/ml. In another refinement, vitamins are present in an amount from about 0.001 g/ml to about 0.005 g/ml. In still another refinement, vitamins are present in an amount from about 0.0010 g/ml to about 0.0025 g/ml.

As set forth above, the energy composition may include vitamin B6. In a refinement, the B6 is present in an amount from about 0.0001 g/ml to about 0.003 g/ml. In another refinement, the B6 is present in an amount from about 0.0003 g/ml to about 0.002 g/ml. In still another refinement, the B6 is present in an amount from about 0.0006 g/ml to about 0.0009 g/ml.

As set forth above, the energy composition may include vitamin B12. In a refinement, the B12 is present in an amount from about 0.000001 g/ml to about 0.00003 g/ml. In another refinement, the B12 is present in an amount from about 0.000003 g/ml to about 0.00002 g/ml. In still another refinement, the B12 is present in an amount from about 0.000006 g/ml to about 0.00001 g/ml.

As set forth above, the energy composition may include niacinamide or a derivative thereof. In a refinement, the niacinamide or a derivative thereof is present in an amount from about 0 g/ml to about 0.003 g/ml. In a refinement, the niacinamide or a derivative thereof is present in an amount from about 0.0001 g/ml to about 0.003 g/ml. In another refinement, the niacinamide or a derivative thereof is present in an amount from about 0.0003 g/ml to about 0.002 g/ml. In still another refinement, the niacinamide or a derivative thereof is present in an amount from about 0.0006 g/ml to about 0.0009 g/ml.

As set forth above, the energy composition may include folk acid. In a refinement, the folk acid is present in an amount from about 0 g/ml to about 0.0002 g/ml. In a refinement, the folic acid is present in an amount from about 0.000005 g/ml to about 0.0002 g/ml. In another refinement, the folic acid is present in an amount from about 0.00001 g/ml to about 0.00008 g/ml. In still another refinement, the folic is present in an amount from about 0.00002 g/ml to about 0.00004 g/ml.

The energy composition of the present embodiment includes one or more flavorants and/or sweeteners. Characteristically, there are a sufficient number of flavorants and/or sweeteners so that unpalatable tasting components will be masked. Such masking is particularly necessary for caffeine and citicoline. In a refinement of the present invention, the flavorants are present in an amount from about 0 g/ml to about 0.008 g/ml. In another refinement of the present invention, the flavorants are present in an amount from about 0.001 g/ml to about 0.008 g/ml. Sucralose is an example of a sweetener that may be used in the present embodiment. In a refinement, sucralose is present in an amount from about 0 to about 0.004 g/ml. In a refinement, sucralose is present in an amount from about 0.0005 to about 0.004 g/ml. In a refinement, sucralose is present in an amount from about 0.0008 to about 0.003 g/ml. In still another refinement, sucralose is present in an amount from about 0.001 to about 0.002 g/ml. Ethylene diamine tetraacetic acid ("EDTA") may also be included in the present embodiment to improve flavor. In a refinement, EDTA is present in an amount from about 0.00002 g/ml to about 0.00009 g/ml. In another refinement, the EDTA is present in an amount from about 0.00003 g/ml to about 0.00007 g/ml. In still another refinement, the EDTA is present in an amount from about 0.00004 g/ml to about 0.00006 g/ml. In still another refinement, the EDTA is present in an amount from about 0.00002 g/ml to about 0.00003 g/ml. The energy composition also includes one or more fruit flavorants. Such fruit flavorants include, but are not limited to lemon lime flavors, orange flavors, berry flavors, high fructose corn syrup, raspberry juice concentrates, berry juice concentrates and the like.

In another variation of the present embodiment, the energy composition further comprises one or more amino acids or amino acid derivatives. Examples of amino acids or derivatives thereof, include, but are not limited to, N-acetyl L-tyrosine, L-phenylalanine, taurine, and combinations thereof. In a refinement, amino acids or derivatives thereof are present in an amount from about 0.005 to about 0.05 g/ml. In a refinement, amino acids or derivatives thereof are present in an amount from about 0.01 to about 0.04 g/ml. In still another refinement, amino acids or derivatives thereof are present in an amount from about 0.01 to about 0.03 g/ml.

In a refinement, N-acetyl L-tyrosine is present in an amount from about 0.001 to about 0.008 g/ml. In a refinement, N-acetyl L-tyrosine is present in an amount from about 0.002 to about 0.006 g/ml. In still another refinement, N-acetyl L-tyrosine is present in an amount from about 0.003 to about 0.005 g/ml.

In a refinement, L-phenylalanine is present in an amount from about 0.001 to about 0.008 g/ml. In a refinement, L-phenylalanine is present in an amount from about 0.002 to about 0.006 g/ml. In still another refinement, L-phenylalanine is present in an amount from about 0.003 to about 0.005 g/ml.

In a refinement, taurine is present in an amount from about 0.002 to about 0.016 g/ml. In a refinement, taurine is present in an amount from about 0.004 to about 0.012 g/ml. In still another refinement, taurine is present in an amount from about 0.007 to about 0.010 g/ml.

In still another variation of the present embodiment, the energy composition of the present invention further includes additional components that reduce fatigue. Such additional components include, for example glucuronolactone. In a refinement, glucuronolactone is present in an amount from about 0.001 to about 0.012 g/ml. In a refinement, glucuronolactone is present in an amount from about 0.003 to about 0.0009 g/ml. In still another refinement, glucuronolactone is present in an amount from about 0.005 to about 0.007 g/ml.

In still another variation of the present invention, the energy composition further includes one or more pH-modifying components. In one refinement, the pH-modifying components are acidulants. Typically, such pH-modifying components are inorganic acids or edible organic acids such as italic acid and citric acid. In a refinement, the pH-modifying components are present in an amount from about 0.001 to about 0.012 g/ml. In a refinement, the pH-modifying components are present in an amount from about 0.003 to about 0.0009 g/ml. In still another refinement, the pH-modifying components are present in an amount from about 0.005 to about 0.007 g/ml.

In still another variation of the present invention, the energy composition includes added fiber. Cellulose is an example of a fiber that may be used in the present variation.

In still another variation of the present embodiment, the energy composition further includes one or more enzymes. Examples of such enzymes include, but are not limited to, amylase, protease, lactase, lipase, cellulase, and combinations thereof.

In yet another variation of the present invention, the energy composition further comprises a preservative. In a refinement, the preservative is a natural preservative. Examples of useful preservatives include, but are not limited to, benzoic acid and benzoic acid derivatives such as sodium benzoate, calcium benzoate, potassium benzoate, magnesium benzoate, and combinations thereof; and sorbic acid derivatives such as potassium sorbate. In a refinement, the preservative is present in an amount from about 0 to about 0.01 g/ml. In a refinement, the preservative is present in an amount from about 0.001 to about 0.008 g/ml. In still another refinement, the preservative is present in an amount from about 0.004 to about 0.006 g/ml.

The compositions of the present invention are made by introducing suitable amounts of the ingredients set forth above into a suitable edible liquid. Water is a particularly useful liquid for this purpose. Tables 1-4 provide a set of components that may be introduced into such a liquid. The amounts provided in tables 1-4 are particularly useful to form compositions having a total final volume of about 60 ml.

TABLE 1

Edible Energy Compositions

| Component | Amounts (mg) |
|---|---|
| Caffeine | 80-220 |
| Citicoline | 5-30 |
| Vitamins | |
| B6 | 20-60 |
| B12 | 0.30-0.70 |
| Niacinamide | 0-60 |
| Folic Acid | 0-5 |
| Glucuronolactone | 200-600 |
| Amino Acids | |
| N-Acetyl L-Tryosine | 150-500 |
| L-Phenylalanine | 150-400 |
| Taurine | 300-800 |
| Malic Acid | 200-500 |
| Flavorants | 0-400 |
| Preservatives | |
| sodium benzoate | 0-150 |
| potassium sorbate | 0-150 |
| Sweeteners | |
| sucralose | 0-150 |

TABLE 2

Edible Energy Compositions

| Component | Amounts (mg) |
|---|---|
| Caffeine | 100-200 |
| Citicoline | 10-25 |
| Vitamins | |
| B6 | 35-45 |
| B12 | 0.50 |
| Niacinamide | 35-45 |
| Folic Acid | 0.1-0.7 |
| Glucuronolactone | 300-500 |
| Amino Acids | |
| N-Acetyl L-Tryosine | 200-400 |
| L-Phenylalanine | 200-400 |
| Taurine | 350-700 |
| Malic Acid | 250-400 |
| Flavorants | 200-350 |
| Preservatives | |
| sodium benzoate | 25-75 |
| potassium sorbate | 25-75 |
| Sweeteners | |
| sucralose | 55-75 |

TABLE 3

Edible Energy Compositions

| Component | Amounts (mg) |
|---|---|
| Caffeine | 100-250 |
| Citicoline | 10-50 |
| Vitamins | |
| B6 | 20-60 |
| B12 | 0.30-0.70 |
| Niacinamide | 0-60 |
| Folic Acid | 0-5 |
| Glucuronolactone | 200-600 |
| Amino Acids | |
| N-Acetyl L-Tryosine | 150-500 |
| L-Phenylalanine | 150-400 |
| Taurine | 300-800 |
| Malic Acid | 200-500 |
| Flavorants | 0-400 |
| Preservatives | |
| sodium benzoate | 0-150 |
| potassium sorbate | 0-150 |
| Sweeteners | |
| sucralose | 0-150 |

TABLE 4

| Edible Energy Compositions | |
|---|---|
| Component | Amounts (mg) |
| Caffeine | 120-230 |
| Citicoline | 20-45 |
| Vitamins | |
| B6 | 35-45 |
| B12 | 0.25-0.75 |
| Niacinamide | 35-45 |
| Folic Acid | 1-2 |
| Glucuronolactone | 300-500 |
| Amino Acids | |
| N-Acetyl L-Tryosine | 200-400 |
| L-Phenylalanine | 200-400 |
| Taurine | 350-700 |
| Malic Acid | 250-400 |
| Flavorants | 200-350 |
| Preservatives | |
| sodium benzoate | 25-75 |
| potassium sorbate | 25-75 |
| Sweeteners | |
| sucralose | 75-100 |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A edible energy composition consisting of:
    a methylated xanthine in an amount from about 0.0005 g/ml to about 0.005 g/ml;
    a choline derivative in an amount from about 0.00005 g/ml to about 0.0009 g/ml;
    an edible organic acid;
    Sucralose;
    an ingredient selected from the group consisting of vitamins, glucuronolactone, N-acetyl-tyrosine, L-phenylalanine, taurine and combinations thereof; and
    a preservative.

2. The edible energy composition of claim 1 wherein said vitamins are present in an amount from 0.0005 g/ml to about 0.008 g/ml.

3. The edible energy composition of claim 1 comprising vitamin B6 in an amount from about 0.0001 g/ml to about 0.003 g/ml; vitamin B12 in an amount from about 0.000001 g/ml to about 0.00003 g/ml; folic acid in an amount from about 0.000005 g/ml to about 0.0002 g/ml; and niacinamide in an amount from about 0.0001 g/ml to about 0.003 g/ml.

4. The edible energy composition of claim 1 wherein said methylated xanthine is caffeine.

5. The edible energy composition of claim 4 wherein said caffeine is present in an amount from about 0.0016 g/ml to about 0.0040 g/ml.

6. The edible energy composition of claim 1 wherein said choline derivative is citicoline.

7. The edible energy composition Of claim 1 wherein said organic acid is malic acid.

8. The edible energy composition of claim 7 said malic acid is present in an amount from about 0.001 to about 0.012 g/ml.

9. The edible energy composition of claim 1 comprising glucuronolactone in an amount from about 0.001 to about 0.012 g/ml.

10. The edible energy composition of claim 1 wherein said preservative is selected from group consisting of sodium benzoate, calcium benzoate, potassium benzoate, magnesium benzoate, potassium sorbate and combinations thereof.

11. The edible energy composition of claim 1 wherein the preservative is a natural preservative.

12. The edible energy composition of claim 1 comprising N-acetyl L-tyrosine in an amount from about 0.001 to about 0.008 g/ml, L-phenylalanine in an amount from about 0.001 to about 0.008 g/ml and taurine in an amount from about 0.001 to about 0.008 g/ml.

13. The edible energy composition of claim 1 comprising vitamin B6; vitamin B12; folic acid; malic acid; niacinamide; glucuronolactone; N-acetyl L-tyrosine and L-phenylalanine.

* * * * *